(12) United States Patent
Peterson et al.

(10) Patent No.: US 10,314,502 B2
(45) Date of Patent: Jun. 11, 2019

(54) SYSTEM AND METHODS FOR SENSING VECTOR SELECTION

(71) Applicant: Cardiac Pacemakers, Inc., St. Paul, MN (US)

(72) Inventors: Les N. Peterson, Woodbury, MN (US); Sunipa Saha, Shoreview, MN (US); Adam MacEwen, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 251 days.

(21) Appl. No.: 15/163,938

(22) Filed: May 25, 2016

(65) Prior Publication Data

US 2017/0000363 A1 Jan. 5, 2017

Related U.S. Application Data

(60) Provisional application No. 62/187,898, filed on Jul. 2, 2015.

(51) Int. Cl.
*A61B 5/00* (2006.01)
*A61B 5/04* (2006.01)
*A61B 5/042* (2006.01)
*A61N 1/365* (2006.01)
*A61N 1/368* (2006.01)
*A61B 5/11* (2006.01)
(Continued)

(52) U.S. Cl.
CPC ........ *A61B 5/04011* (2013.01); *A61B 5/0422* (2013.01); *A61B 5/686* (2013.01); *A61N 1/3684* (2013.01); *A61N 1/36585* (2013.01); *A61B 5/04012* (2013.01); *A61B 5/0468* (2013.01); *A61B 5/0472* (2013.01); *A61B 5/1116* (2013.01); *A61B 5/1118* (2013.01); *A61B 5/7203* (2013.01)

(58) Field of Classification Search
CPC .......................... A61B 5/04011; A61B 5/0422
USPC ....................................................... 600/512
See application file for complete search history.

(56) References Cited

U.S. PATENT DOCUMENTS 6,135,957 A * 10/2000 Cohen-Bacrie ......... G01P 5/244
600/370
6,978,178 B2 12/2005 Sommer et al.
8,200,341 B2 6/2012 Sanghera et al.
(Continued)

*Primary Examiner* — Nadia A Mahmood
(74) *Attorney, Agent, or Firm* — Schwegman Lundberg & Woessner, P.A.

(57) ABSTRACT

Systems and methods for evaluating multiple candidate sensing vectors for use in sensing electrical activity of a heart are disclosed. The system can sense physiologic signals using each of a plurality of candidate sensing vectors, and generate respective signal intensity indicators and interference indicators using the physiologic signals sensed by using the respective sensing vectors. The system can also receive electrode information of each of the candidate sensing vectors, including information about sensing electrodes that are also used for delivering cardiac electrostimulation. The system can rank at least some of the plurality of candidate sensing vectors according to the signal intensity indicators, the interference indicators, and the electrode information. The system can also include a user interface for displaying the ranked sensing vectors, and allowing the user to select at least one sensing vector for use in sensing the cardiac electrical activity.

19 Claims, 5 Drawing Sheets

(51) Int. Cl.
    *A61B 5/0468*    (2006.01)
    *A61B 5/0472*    (2006.01)

(56) References Cited

U.S. PATENT DOCUMENTS

| | | |
|---|---|---|
| 8,788,023 B2 | 7/2014 | Sanghera et al. |
| 9,332,924 B2 | 5/2016 | Thakur et al. |
| 2009/0043351 A1 | 2/2009 | Sathaye et al. |
| 2011/0208261 A1 | 8/2011 | Levine et al. |
| 2012/0157874 A1* | 6/2012 | Thakur ............... A61B 5/0205 600/547 |

* cited by examiner

SYSTEM AND METHODS FOR SENSING VECTOR SELECTION

CLAIM OF PRIORITY

This application claims the benefit of priority under 35 U.S.C. § 119(e) of U.S. Provisional Patent Application Ser. No. 62/187,898, filed on Jul. 2, 2015, which is herein incorporated by reference in its entirety.

TECHNICAL FIELD

This document relates generally to medical devices, and more particularly, to devices and methods for sensing cardiac electrical activity.

BACKGROUND

Congestive heart failure (CHF) is a leading cause of death in the United States. CHF occurs when the heart is unable to adequately supply enough blood to maintain a healthy physiological state. CHF can be treated by drug therapy, or by an implantable medical device (IMD) such as for providing cardiac pacing therapies, including resynchronization therapy (CRT) to correct cardiac dyssynchrony within a ventricle or between ventricles.

The IMD can chronically stimulate excitable tissues or organs, such as a heart, to treat abnormal cardiac rhythms or to help improve cardiac performance in a patient with CHF. Such ambulatory medical devices can have at least first and second electrodes that can be positioned within the heart or on a surface of the heart for contacting the cardiac tissue. The electrodes can be electrically coupled to an electronics unit such as a pulse generator, such as via a lead, and can be used to deliver one or more electrostimulations to the heart, such as to restore or to improve the normal heart function.

The IMD can also sense cardiac signals using the electrodes on one or more leads. The cardiac signals can be sensed as a voltage signal across two sensing electrodes. Depending on the location of the sensing electrodes, the IMD can sense various cardiac electrical events such as depolarization of a heart chamber, such as an atrium or a ventricle. Proper sensing of cardiac electrical events can provide useful diagnostic information including progression of a cardiac disease, such as worsening of CHF, and be used to determine cardiac therapies such as cardiac pacing including the CRT therapies.

OVERVIEW

Cardiac stimulation using an implantable medical device (IMD) can involve one or more implantable leads that can be transvascularly inserted into one of the heart chambers, such as an atrium or a ventricle. Stimulation of the heart can be accomplished through direct myocardium stimulation using at least first and second electrodes that can be electrically connected to the IMD and in close contact with the cardiac tissue. The electrodes can be positioned along the one or more implantable leads. The stimulation can be provided at specified stimulation strength (e.g., stimulation energy) sufficient to capture the heart tissue, that is, the stimulation can effectively cause depolarization propagating to a part or the entirety of the heart.

During the CRT therapy, synchronized stimulation can be applied to the left ventricle (LV) and the right ventricle (RV) of a heart. Conventionally, there can be one RV pacing site and one LV pacing site. Stimulation of multiple sites on a chamber of the heart, such as pacing at multiple LV sites (which is known as multi-site LV pacing), has been proposed as an alternative to the conventional single site CHF therapy. Compared to the CRT therapy with single site LV pacing, multi-site LV pacing can be more beneficial to some patients at least due to its more effective recruitment of excitable cardiac tissues. Such benefits can include improved cardiac hemodynamic outcome in some CHF patients.

Proper sensing of cardiac electrical activity is critical for determining the necessity and specific therapies for treating CHF. The cardiac electrical activity can be sensed using a sensing vector that comprises two electrodes, at least one of which is positioned at a portion of the heart where a target cardiac event is to be detected. The electrodes can be positioned at the endocardial or epicardial surface of an atrium or a ventricle. Generally, an ideal sensing vector should provide sufficiently large amplitude for a sensing circuit to sense a depolarization of a portion of the heart. However, many factors may negatively impact the quality of the sensed cardiac electrical signal, resulting in under-sensing or over-sensing of cardiac electrical activity. In an example of sensing electrical activity of the LV, under-sensing of intrinsic LV electrical activity can cause the IMD to deliver extra pacing pulses, which provides no therapeutic benefit and may have potential proarrhythmic effects, in addition to battery depletion. On the other hand, over-sensing of intrinsic LV electrical activity can results in unintended inhibition of LV pacing or CRT therapy, which can cause deterioration of cardiac function.

Some IMD systems can be designed to have more electrodes available such as for the purpose of multisite pacing. Multi-electrode implantable leads or catheters, or multiple leads, can be implanted for multisite LV pacing. These multiple electrodes can also be used to construct a variety of potential sensing vectors. Poor sensing signal quality and the resultant problems of oversensing or undersensing associated with one sensing vector can be mitigated by choosing a relatively "optimal" sensing vector from the candidate sensing vectors. This generally requires that clinicians run multiple tests on various candidate sensing vectors, and compare the respective performances of the candidate sensing vectors. However, such a process of selecting "optimal" sensing vectors can be especially burdensome with a larger pool of candidate sensing vectors. The present inventors have recognized, among other things, that there remains a demand for systems and methods that can provide a more efficient process of evaluating multiple candidate sensing vectors, and identifying one or more vectors with higher signal quality and less interference.

This document discusses, among other things, a system for evaluating a plurality of candidate sensing vectors for use in sensing electrical activity of a heart. The system can sense physiologic signals using a specified sensing vector, and analyze the physiologic signals to generate a signal intensity indicator and an interference indicator. The system can receive respective signal intensity indicators and the respective interference indicators generated from respective physiologic signals sensed by using the plurality of candidate sensing vectors. The system can also receive electrode information of each of the candidate sensing vectors, including information about electrodes that are also used for delivering cardiac electrostimulation. The system can rank at least some of the plurality of candidate sensing vectors using the respective signal intensity indicators, the respective interference indicators, and the electrode information.

Example 1 can include a system that comprises a sensing circuit that can sense one or more physiologic signals indicative of target cardiac electrical activity according to a specified sensing vector. The sensing vector can involve first and second electrodes. A signal processor circuit can generate a signal intensity indicator and an interference indicator using the one or more physiologic signals. The signal intensity indicator can be indicative of the strength of the sensed one or more physiologic signals, and the interference indicator can be indicative of presence or degree of interference produced by an activity other than the target cardiac electrical activity. The system can include a sensing vector assessment circuit that can receive respective signal intensity indicators and the respective interference indicators corresponding to the plurality of candidate sensing vectors. The sensing vector assessment circuit can also receive respective electrode information of the plurality of candidate sensing vectors. The respective electrode information can include respective first or second electrode being also used for delivering cardiac electrostimulation. The sensing vector assessment circuit can produce a rankable set of at least some of the plurality of candidate sensing vectors using the respective signal intensity indicators, the respective interference indicators, and the respective electrode information.

Example 2 can include, or can optionally be combined with the subject matter of Example 1 to optionally include, the sensing vector assessment circuit that can generate first ranked vectors by ranking the at least some of the plurality of candidate sensing vectors according to a first specified order of one or both of the respective signal intensity indicators and the respective interference indicators. The sensing vector assessment circuit can identify a portion of the first ranked vectors with corresponding respective signal intensity indicators or corresponding respective interference indicators meeting a specified condition. The sensing vector assessment circuit can also generate second ranked vectors by ranking the identified portion of the first ranked vectors according to a second specified order based on the respective electrode information.

Example 3 can include, or can optionally be combined with the subject matter of Example 2 to optionally include, the sensing vector assessment circuit that can generate the first ranked vectors according to a descending order of the respective signal intensity indicators or an ascending order of the respective interference indicators.

Example 4 can include, or can optionally be combined with the subject matter of one or any combination of Examples 2 or 3 to include, the sensing vector assessment circuit than can generate the second ranked vectors according an ascending order of the number of electrodes also used for delivering cardiac electrostimulation.

Example 5 can include, or can optionally be combined with the subject matter of Example 1 to optionally include, the sensing vector assessment circuit that can generate respective composite scores using the respective signal intensity indicator for at least some of the plurality of candidate sensing vectors, the respective interference indicators, and the electrode information. The sensing vector assessment circuit can rank the at least some of the plurality of candidate sensing vectors in a specified order of the respective composite scores.

Example 6 can include, or can optionally be combined with the subject matter of one or any combination of Examples 1 through 5 to include, a user interface unit that can display the ranked sensing vectors, the corresponding respective signal intensity indicators, and the corresponding respective interference indicators. The user interface unit can also receive a user input, including selecting at least one sensing vector from the ranked sensing vectors and programming the sensing circuit to sense the target cardiac electrical activity using the selected at least one sensing vector.

Example 7 can include, or can optionally be combined with the subject matter of one or any combination of Examples 1 through 6 to include, the sensing vector assessment circuit that can automatically select at least one sensing vector from the ranked sensing vectors. The sensing circuit can sense the target cardiac electrical activity according to the selected at least one sensing vector.

Example 8 can include, or can optionally be combined with the subject matter of one or any combination of Examples 1 through 7 to include, the signal processor circuit that can produce at least a signal metric using the one or more physiologic signals, and generate the signal intensity indicators including one or more of a central tendency measure or a variability of the signal metric over a specified period of time.

Example 9 can include, or can optionally be combined with the subject matter of one or any combination of Examples 1 through 8 to include, a sensor configured to sense a physical activity level or a posture of a patient. The signal processor circuit is configured to generate the variability of the signal metric during multiple physical activity levels or postures.

Example 10 can include, or can optionally be combined with the subject matter of Example 9, the sensor for sensing the physical activity level or the posture of a patient, which can include one or more of a tilt switch, an accelerometer, or an impedance sensor.

Example 11 can include, or can optionally be combined with the subject matter of one or any combination of Examples 1 through 10 to include, the signal processor circuit that can generate the interference indicators including one or more of a noise level, a signal-to-noise ratio (SNR), or presence or intensity of far-field electrical activity of a portion of the heart.

Example 12 can include, or can optionally be combined with the subject matter of one or any combination of Examples 1 through 11 to include, a plurality of candidate sensing vectors including two or more LV sensing vectors each involving at least one electrode removably and respectively positionable at an LV of the heart. The sensing circuit can sense respective LV electrograms using the two or more LV sensing vectors.

Example 13 can include, or can optionally be combined with the subject matter of Example 12, at least one lead or catheter configured to be positioned to the LV, the at least one lead or catheter including two or more electrodes configured to form the two or more LV sensing vectors Example 14 can include, or can optionally be combined with the subject matter of one or any combination of Examples 12 or 13 to include, the signal processor circuit that can generate the signal intensity indicator and the interference indicator using the sensed LV electrogram. The interference indicator can include presence or significance of far-field atrial electrical activity in the sensed LV electrogram.

Example 15 can include, or can optionally be combined with the subject matter of one or any combination of Examples 12 through 14 to include, the sensing vector assessment circuit that can generate the first ranked vectors according to one or both of a descending order of the signal intensity indicators and an ascending order of the interference indicators, and generate the second ranked vectors according to an ascending order of the number of electrodes also used for delivering cardiac electrostimulation to the LV.

Example 16 can include, or can optionally be combined with the subject matter of one or any combination of Examples 1 through 15 to include, a therapy circuit configured to deliver a therapy using the ranked candidate sensing vectors.

Example 16 can include a method for evaluating a plurality of candidate sensing vectors for use in sensing electrical activity of a heart. The method can comprise steps of sensing one or more physiologic signals indicative of target cardiac electrical activity according to each of the plurality of candidate sensing vectors involving first and second electrodes, and generating from the one or more physiologic signals respective signal intensity indicators and respective interference indicators. The respective signal intensity indicators can be indicative of the strength of the sensed one or more physiologic signals, and the respective interference indicators can be indicative of presence or degree of interference produced by an activity other than the target cardiac electrical activity. The method can include receiving respective electrode information for each of the plurality of candidate sensing vectors. The respective electrode information can include the first or second electrode being also used for delivering cardiac electrostimulation. The method can include ranking at least some of the plurality of candidate sensing vectors using the respective signal intensity indicators, the respective interference indicators, and the respective electrode information.

Example 17 can include, or can optionally be combined with the subject matter of Example 16, to optionally include an operation of generating first ranked vectors by ranking the at least some of the plurality of candidate sensing vectors according to a first specified order of one or both of the respective signal intensity indicators and the respective interference indicators, identifying a portion of the first ranked vectors with corresponding respective signal intensity indicators or corresponding respective interference indicators meeting a specified criterion, and generating second ranked vectors by ranking the identified portion of the first ranked vectors according to a second specified order based on the electrode information.

Example 18 can include, or can optionally be combined with the subject matter of Example 16 to optionally include, for at least some of the plurality of candidate sensing vectors, generating respective composite scores using the respective signal intensity indicators, the respective interference indicators, and the electrode information, and ranking the at least some of the plurality of candidate sensing vectors in a specified order of the respective composite scores.

Example 19 can include, or can optionally be combined with the subject matter of Example 16 to optionally include, displaying in a user interface unit the ranked sensing vectors, the respective signal intensity indicators, and the respective interference indicators. Example 19 can also include a method of receiving a user input including selecting at least one sensing vector from the ranked sensing vectors and programming the sensing circuit to sense the target cardiac electrical activity according to the selected at least one sensing vector.

Example 20 can include, or can optionally be combined with the subject matter of Example 16 to optionally include, generating the signal intensity indicators that can include producing at least a signal metric using the one or more physiologic signals, and determining one or more of a central tendency measure, or a variability, of the signal metric over a specified period of time.

Example 21 can include, or can optionally be combined with the subject matter of Example 20 to optionally include, sensing a physical activity level or a posture of a patient. The signal intensity indicators can include variability of the signal metric during multiple physical activity levels or postures.

Example 22 can include, or can optionally be combined with the subject matter of Example 16 to optionally include, generating the interference indicators that can include determining one or more of a noise level, a signal-to-noise ratio (SNR), or presence or intensity of far-field electrical activity of a portion of the heart.

Example 23 can include, or can optionally be combined with the subject matter of Example 16, to optionally include, a plurality of candidate sensing vectors including two or more LV sensing vectors each involving at least one electrode removably and respectively positionable at an LV of the heart. Example 23 can also include sensing respective LV electrograms using the two or more LV sensing vectors, generating the first ranked vectors according to one or both of a descending order of the signal intensity indicators and an ascending order of the interference indicators, and generating the second ranked vectors according to an ascending order of the number of electrodes also used for delivering cardiac electrostimulation to the LV.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for evaluating and ranking multiple candidate sensing vectors used for sensing cardiac electrical activity. For each of the candidate sensing vectors, one or more physiologic signals, such as an electrogram, can be sensed, and a number of signal indicators, interference indicators can be produced using the respective physiologic signals. The multiple candidate sensing vectors can be ranked according to one or more of the indicators and electrode information in a specified order. At least one sensing vector can be selected from the ranked list of candidate vectors. The selected sensing vector can be programmed to a device or system for sensing future cardiac electrical activity.

Figure 1:
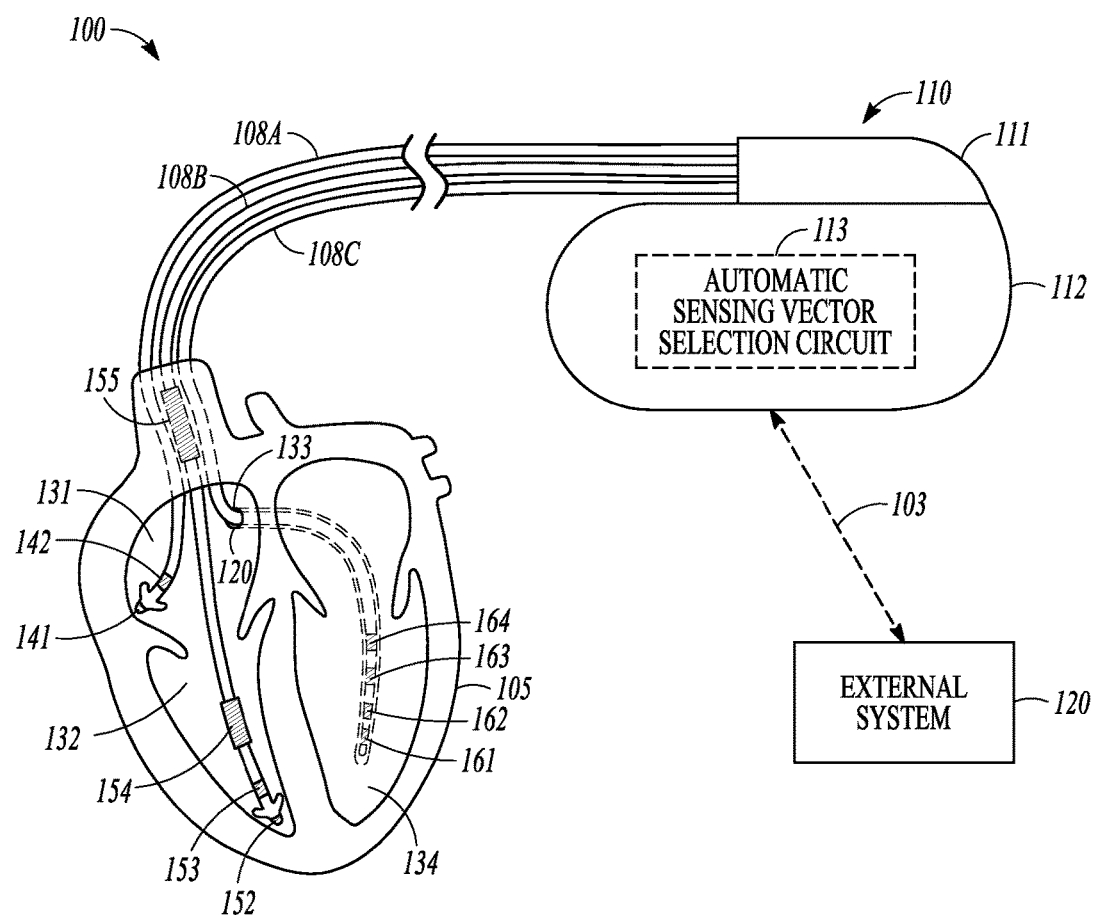
FIG. 1 illustrates generally an example of a Cardiac Rhythm Management (CRM) system and portions of an environment in which the CRM system can operate.

FIG. 1 illustrates generally an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMB 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing the LV electrogram and optionally allow delivery of one or more resynchronization pacing pulses from the LV. Additional electrodes can be included in or along the lead 108C. In an example, as illustrated in FIG. 1, a third electrode 163 and a fourth electrode 164 can be included in the lead 108. In some examples (not shown in FIG. 1), at least one of the leads 108A-C, or an additional lead other than the leads 108A-C, can be implanted under the skin surface without being within at least one heart chamber, or at or close to heart tissue.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMB 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMB 110 can also be configured to sense a physiological signal from one or more external physiologic sensors or one or more external electrodes that can be coupled to the IMB 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include an automatic sensing vector selection circuit 113. The automatic sensing vector selection circuit 113 can sense a target cardiac electrical activity at one or more sites in at least one chamber of the heart 105. As an example, the automatic sensing vector selection circuit 113 can sense intrinsic depolarization of the left ventricle (LV) 134, such as by using a plurality of sensing vectors each involving one or more of LV electrodes such as electrodes 161-164 on the implantable lead 108C. The automatic sensing vector selection circuit 113 can use the sensed cardiac electrical signal to produce a signal intensity indicator indicative of the strength of sensed cardiac electrical activity, and a noise or interference indicator indicative of presence or degree of noise or interference in the sensed cardiac electrical signal. Additionally or alternatively, the automatic sensing vector selection circuit 113 can receive electrode information of each of the plurality of candidate sensing vectors, including number of sensing electrodes in that sensing vector which are also used for delivering cardiac electrostimulation. The automatic sensing vector selection circuit 113 can rank the candidate sensing vectors in a specified order according to one or more of the respective signal intensity indicators, the noise or interference indicators, and the electrode information. The IMD 110 can be programmed to sense the target cardiac electrical activity using at least one sensing vector selected from the ranked candidate sensing vectors. Examples of the automatic sensing vector selection circuit 113 are described below, such as with reference to FIGS. 2-4.

The external system 120 can allow for programming of the IMB 110 and can receive information about one or more signals acquired by IMB 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMB operational status stored in the IMD 110, one or more programming instructions to the IMB 110 such as to configure the IMB 110 to perform one or more actions that can include physiological data acquisition such as using programmably specifiable sensing electrodes and configuration, device self-diagnostic test, or delivery of one or more therapies.

The automatic sensing vector selection circuit 113 can be implemented at the external system 120 such as using data extracted from the IMB 110 or data stored in a memory within the external system 120. Portions of the automatic sensing vector selection circuit 113 may be distributed between the IMD 110 and the external system 120.

Portions of the IMD 110 or the external system 120 can be implemented using hardware, software, or any combination of hardware and software. Portions of the IMB 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
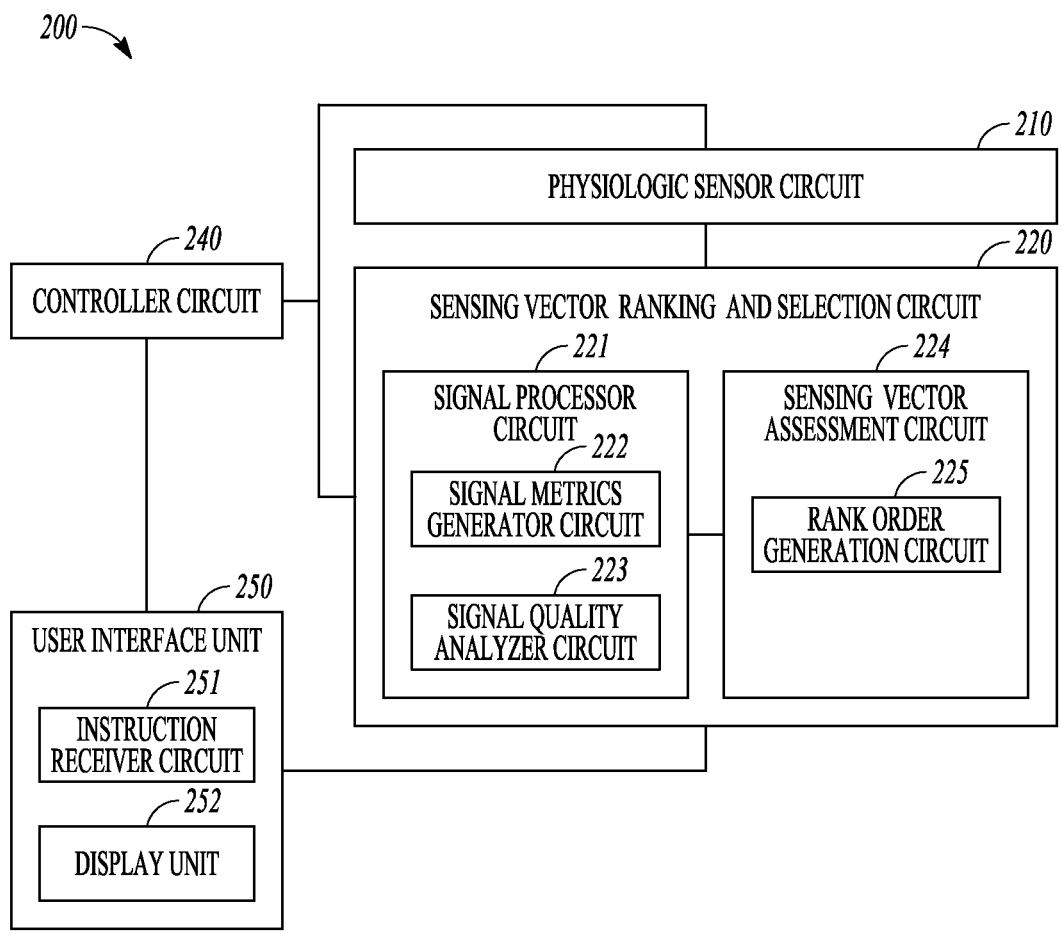
FIG. 2 illustrates generally an example of an automatic sensing vector selection circuit.

FIG. 2 illustrates generally an example of an automatic sensing vector selection circuit 200, which can be an embodiment of the automatic sensing vector selection circuit 113. The automatic sensing vector selection circuit 200 can include one or more of an physiologic sensor circuit 210, a sensing vector ranking and selection circuit 220, a controller circuit 240, and a user interface unit 250.

The physiologic sensor circuit 210 can sense a physiologic signal indicative of a target cardiac electrical activity, such as depolarization of at least a portion of the heart or a heart chamber. The physiologic signal can be sensed using one or more physiologic sensors or electrodes deployed at or near the heart and electrically coupled to the physiologic sensor circuit 210. In an example, the physiologic sensor circuit 210 can be electrically coupled to electrodes non-invasively attached to the body surface to sense electrocardiograms (ECGs), subcutaneous electrodes to sense subcutaneous ECGs, or implantable electrodes such as on one or more implantable leads 108A-C or the IMD can 112 to sense intracardiac electrograms (EGMs) of a chamber of the heart. In a specific example, the physiologic sensor circuit 210 can sense two or more intracardiac EGMs from respective sensing vectors each including at least one of LV electrodes 161-164 (which are hereinafter referred to as LV electrodes "LV1", "LV2", "LV3" and "LV4" electrodes). The LV sensing vector can be a unipolar LV sensing vector which can involve one LV electrode and a reference electrode such as the IMD can 112, or a bipolar sensing vector which can involve any two of the LV electrodes 161-164. The bipolar sensing vector can alternatively involve an LV electrode and an electrode positioned on a different chamber or on a different lead, such as one of electrodes 152-155 on the RV lead 108B, or electrodes 141 or 142 on the RA lead 108A. The physiologic sensor circuit 210 can process the sensed physiologic signals including amplification, digitization, filtering, or other signal conditioning processes.

The sensing vector ranking and selection circuit 220 can be configured to evaluate a plurality of candidate sensing vectors for use in sensing electrical activity of a heart. The sensing vector ranking and selection circuit 220 can be implemented as a part of a microprocessor circuit within the automatic sensing vector selection circuit 200. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the functions, methods, or techniques described herein.

The sensing vector ranking and selection circuit 220 can include a signal processor circuit 221 and a sensing vector assessment circuit 224. The signal processor circuit 221 can include a signal metrics generator circuit 222 and a signal quality analyzer circuit 223. The signal metrics generator circuit 222 can generate one or more signal metrics using the sensed one or more physiologic signals, such as produced by the physiologic sensor circuit 210 or received from a storage device such as an electronic medical record (EMR) system that stores patient's physiologic signals.

The signals metrics can be temporal or morphological features derived from the physiological signals. Examples of the signal metrics can include: intensities (such as amplitudes) and timing of P wave, Q wave, R wave, QRS complex, or T wave detected from a surface ECG or a subcutaneous ECG; timing of sensed activation of at least a portion of a chamber of the heart such as RA, RV, and LV, obtained from the intracardiac EGMs; QRS width; electrical delay of a chamber of the heart such as LV electrical delay; interventricular conduction delay measured as the delay between LV activation to RV activation (LV-RV) delay; intraventricular delay; Q wave to left ventricle activation (Q-LV) interval; among others.

The signal quality analyzer circuit 223 can use one or more signal metrics to generate one or more indicators of signal quality, noise level, or interference. In an example, the signal quality analyzer circuit 223 can generate a signal intensity indicator indicative of the strength of sensed cardiac electrical activity, and an interference indicator indicative of presence or degree of noise or interference in the sensed cardiac electrical signal. Examples of the signal intensity indicator and the noise or interference indicator are discussed below, such as with reference to FIG. 3.

The sensing vector assessment circuit 224, electrically coupled to the signal quality analyzer circuit 223, can receive respective signal intensity indicators and the respective interference indicators corresponding to each of a plurality of candidate sensing vectors. The sensing vector assessment circuit 224 can include a rank order generation circuit 225 that can produce a rankable set of at least some of the candidate sensing vectors using at least the respective signal intensity indicators and the respective noise or interference indicators.

The rank order generation circuit 225 can automatically, or upon receiving a user command such as via the user interface unit 250, perform ranking of the candidate sensing vectors. In an example, the rank order generation circuit 225 can perform multi-level ranking on at least some of the candidate sensing vectors. In an example, the rank order generation circuit 225 can generate first ranked vectors by ranking at least some of the plurality of candidate sensing vectors according to a first specified order of one of the respective signal intensity indicators or the respective interference indicators. The rank order generation circuit 225 can identify a portion of the first ranked vectors with corresponding respective signal intensity indicators or corresponding respective interference indicators meeting a specified condition, such as falling within a specified range. The rank order generation circuit 225 can then generate second ranked vectors by ranking the identified portion of the first ranked vectors according to a second specified order of the other of the respective signal intensity indicators or the respective interference indicators. In an example, the rank order generation circuit 225 can first rank the candidate sensing vectors according to a descending order of the signal intensity indicators, and then rank the ordered sensing vectors (which are produced by the first ranking) according to an ascending order of the interference indicators.

In addition to or in lieu of the multi-level ranking, the sensing vector assessment circuit 224 can generate, for the candidate sensing vectors, respective composite scores using at least the signal intensity indicators and the noise or interference indicators, and rank the candidate sensing vectors according to the composite scores in a specific order. In an example, each signal metric generated by the signal metric generator circuit 222 can be assigned a numerical or categorical score indicative of sensing efficacy. For example, a score for the amplitude of intrinsic cardiac depolarization can be a number between 0 and 10, where a higher score corresponds to a higher amplitude. The composite score can then be computed using a fusion of the scores of the signal metrics. In another example, two or more signal metrics associated with signal strength can be combined to form an aggregated score of signal intensity indicator, and two or more metrics associated with noise or interference can be combined to form an aggregated score of noise or interference indicator. The aggregated score of signal intensity indicator and the aggregated score of noise or interference indicator can each have a respective numerical value, such as between 0 and 10, or a descriptive categorical value such as one or more of "very low", "low", "medium", "high", "very high", which respectively indicate overall signal quality or overall significance of interference. The composite score can then be computed using a fusion of the aggregated score of signal intensity indicators and the aggregated score of noise or interference indicators. Examples of the fusion algorithm can include decision trees, weighted averages, neural networks, or any other linear or non-linear algorithms.

The controller circuit 240 can control the operations of the physiologic sensor circuit 210, the sensing vector ranking and selection circuit 220, and the data flow and instructions between these components and respective subcomponents. The controller circuit 240 can receive from user input such as via the user interface unit 250, or retrieve from a memory of the automatic sensing vector selection circuit 200, a plurality of candidate sensing vectors. For each of the plurality of candidate sensing vectors, the controller circuit 240 can configure the physiologic sensor circuit 210 to sense the physiologic signals, and configure the signal processor circuit 221 to generate respective signal intensity indicators and respective noise or interference indicators. The controller circuit 240 can further configure the sensing vector assessment circuit 224 to rank the candidate sensing vectors according to the signal intensity indicators and the noise and interference indicators in a specified order such as provided by a system user, such as a clinician, via the user interface unit 250.

The user interface unit 250 can include an instruction receiver circuit 251 and a display unit 252. In an example, at least a portion of the user interface unit 250 can be implemented in the external system 120. The instruction receiver circuit 251 can include an input device, such as a keyboard, on-screen keyboard, mouse, trackball, touchpad, touch-screen, or other pointing or navigating devices. The input device can enable a system user to program the parameters used for sensing the physiologic signals. The input device can also enable the system user to input, or choose from a set of predetermined options of, factors (e.g., the signal intensity indicators and the noise or interference indicators) and methods for ranking candidate sensing vectors (e.g., an ascending or descending order for each factor, or a sequence of ranking in a multi-level ranking scheme).

The display unit 252 can be configured to display information in one or more human-perceptible medium formats. The displayed information can include device programming, device status such as lead impedance and integrity, amplitude of the sensed signal, noise level, signal-to-noise ratio (SNR), source of interference, level of interference, ranked sensing vectors, signal intensity indicators, and noise or interference indicators, among others. In an example, the ranked sensing vectors, along with one or more signal intensity indicators and noise or interference indicators, can be presented in a table, a chart, a diagram, or any other types of textual, tabular, or graphical presentation formats, which allows the system user to quickly and effectively interpret relative performances of the candidate sensing vectors, and selecting one or more sensing vectors for sensing cardiac electrical activity.

The automatic sensing vector selection circuit 200 can optionally include a vector selection circuit configured to automatically recommend and prompt to the system user at least one sensing vector from the ranked sensing vectors. The display unit 252 can display the recommended sensing vectors using a checkmark, a sign or token, highlight, annotation, or other visual identifier to distinguish from the rest of the sensing vectors. In an example, the display unit 252 can display the recommended sensing vector simultaneously with a pre-existing sensing vector different than the recommended sensing vector, and the controller circuit 240 can switch from the pre-existing sensing vector to the recommended sensing vector either automatically or upon receiving a confirmation from the system user.

In an example, the automatic sensing vector selection circuit 200 can optionally coupled to a therapy circuit, such as included in the IMD 110. The therapy circuit can be configured to deliver a therapy to the patient at least based on a signal sensed using a vector selected from the ranked sensing vectors. Examples of the therapy can include electric pacing therapy, cardioversion therapy, defibrillation therapy, neuromodulation therapy, or other stimulation therapies using a specified energy source. In some examples, the therapy circuit can be configured to receive user instructions, such as from the user interface unit 250, on programming one or more therapy parameters and delivering the programmed therapy to a target site in a patient.

Figure 3:
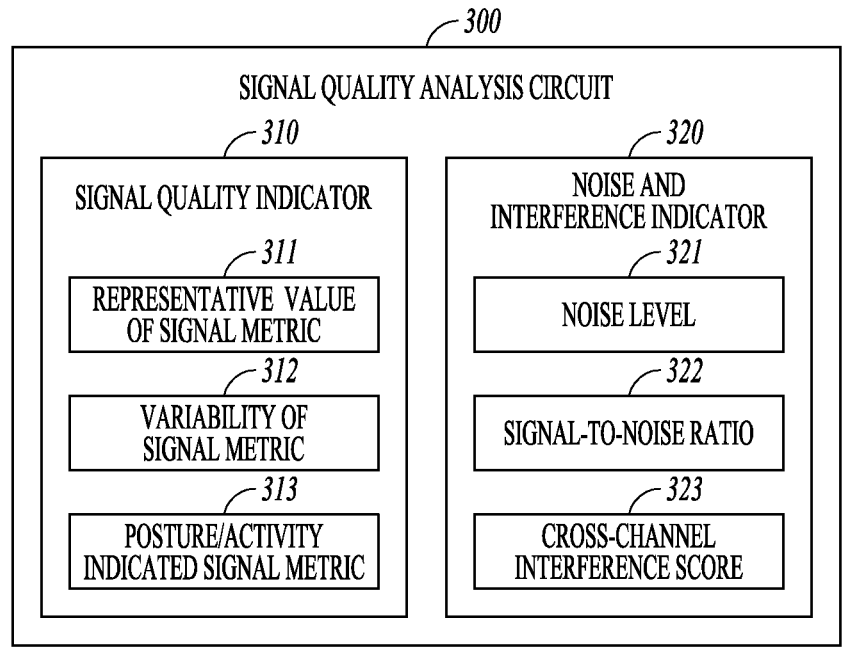
FIG. 3 illustrates generally an example of a signal quality analyzer circuit that can be used for sensing vector selection.

FIG. 3 illustrates generally an example of a signal quality analyzer circuit 300, which can be an embodiment of the signal quality analyzer circuit 223. The signal quality analyzer circuit 300 can produce a signal intensity indicator 310 and a noise or interference indicator 320. The signal intensity indicator and the noise or interference indicator can be used for generating a ranked order of a plurality of sensing vectors for sensing cardiac electrical activity.

The signal intensity indicator can include a first-order, a second-order, or a higher-order statistic of a signal metric computed using multiple measurements of the signal metric over a specified period of time or over a specified number of cardiac cycles. In an example as illustrated in FIG. 3, the signal intensity indicator can include a representative value of the signal metric 311. The representative value can be a first-order static, such as a mean, median, mode, or other measures of central tendency computed over multiple measurements of the signal metric. The signal intensity indicator can additionally include a variability of signal metric 312, such as a variance, standard deviation, range, or other second-order statistic computed over multiple measurements of the signal metric. In some examples, multiple measurements of the signal metric can be obtained over a specified period of time under a specified condition, such as when the heart undergoes normal sinus rhythm, when the heart rate is within a specified range, or during specified time of day.

The signal intensity indicator can further include a posture or physical activity indicated signal metric 313. Changes in activity level can affect the cardiac electrical activity and result in ECG morphology changes. For example, a change from rest to maximal level of exercise can result in an increase in R wave amplitude at submaximal exercise and then reduces to a minimum at maximal exercise, a tall and peaked T wave, an upsloping of ST segment, among others. Such a change may be exaggerated in certain patients with heart diseases, thus resulting in large inter-patient variation. Changes in activity level or changes in postures can also affect the lead and electrode position, and thus the orientation of the sense vectors relative to the heart chamber. In an example, the physiologic sensor circuit 210 signal can sense cardiac electrical signals under different postures or different activity levels such as sensed by a posture or physical activity sensor. The posture or physical activity indicated signal metric 313 can be computed as a variability measure of the signal metric using multiple measurements respectively obtained across multiple physical activity levels or postures. Information of the patient posture or physical activity level can be received from one or more of a tilt switch, a single axis accelerometer, or a multi-axis accelerometer, such as can be disposed in or on a patient body, including information about a patient tilt angle. In another example, patient posture or physical activity information can be discerned from thoracic impedance information, such as by clustering the thoracic impedance information, as described by Thakur et al., in U.S. Patent Application No. 61/423,128, entitled "POSTURE DETECTION USING THORACIC IMPEDANCE", which is herein incorporated by reference in its entirety. The posture or physical activity indicated signal metric can be indicative of robustness of the sensing vector in sensing the cardiac electrical activity under different postures or levels of physical activities.

The noise or interference indicator 320 can include a noise level metric 321 such as noise amplitude or power, or a signal-to-noise ratio (SNR) 322. The noise can include non-physiologic background noise such as electromagnetic interference (EMI), or physiologic noise such as electromyographic noise or spurious electrode or tissue motion artifacts. The noise level or the SNR can be estimated using multiple measurements of the signal metric. The noise or interference indicator 320 can additionally include presence or an intensity of far-field electrical activity produced by a portion of the heart, which is different than the target electrical activity. In an example of ranking LV sense vectors, the far-field electrical activity can include atrial activation signal picked up by a LV sense vector, which is also known as cross-channel interference. The cross-channel interference can be prominent when one of both of the electrodes of the LV sensing vector are positioned in close proximity of an atrium. For example, LV sensing vectors that involve one or two proximal electrodes LV3 or LV4 (electrodes 163 and 164, respectively) of the lead 108C can be more likely to have far-field atrial interference than the LV sensing vectors that involve more distal electrodes LV1 or LV2 (electrodes 161 and 162, respectively). The presence or intensity of the far-field electrical activity can be detected using a comparison of the LV electrogram sensed by the LV sensing vector and the atrial electrogram, such as based on relative timing or morphologic similarity between the LV electrogram and the atrial electrogram.

Figure 4:
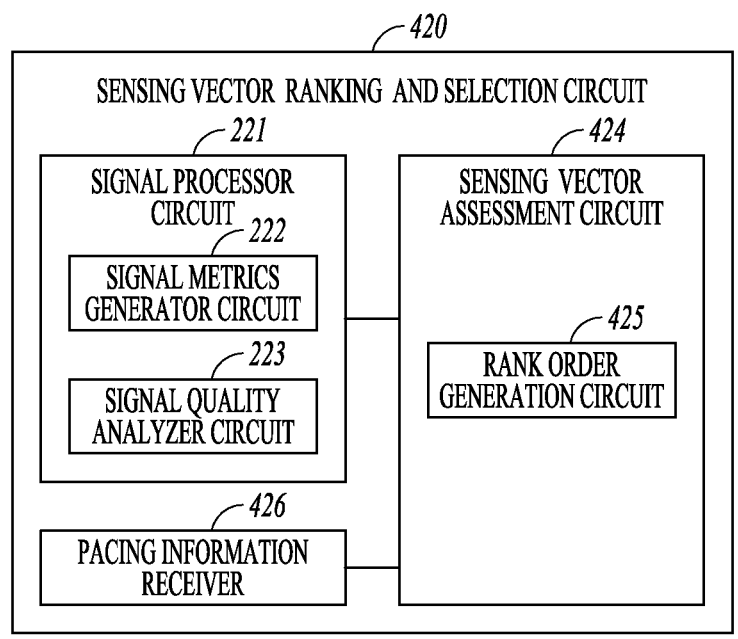
FIG. 4 illustrates generally an example of a sensing vector ranking and selection circuit.

FIG. 4 illustrates generally an example of a sensing vector ranking and selection circuit 420, which can be an embodiment of the sensing vector ranking and selection circuit 220. The sensing vector assessment circuit 420 can include the signal processor circuit 221 as included in the sensing vector ranking and selection circuit 220. Additionally, the sensing vector assessment circuit 420 can include a pacing information receiver 426, which can receive information about the electrodes involved in each of the candidate sensing vectors, where the electrodes are also used for delivering cardiac electrostimulation. An electrostimulation electrode, if used also in a sensing vector for sensing cardiac electrical activity (hereinafter referred to as "shared electrodes"), may cause the sensing circuit to pick up ensuing after-potential of the stimulation pulses and electrode-tissue polarization artifact, thereby resulting in spurious sensing. As such, to minimize stimulation artifacts, it is desirable that the sensing vector do not include "shared electrodes". The pacing information receiver 426 can receive the information about electrostimulation electrodes from a user input such as via the user interface unit 250, or retrieve the information from a memory where the present configurations of the electrostimulation vectors are stored.

The sensing vector assessment circuit 424 can receive respective stimulation efficacy indicators and the noise or interference indicators from the signal quality analyzer circuit 223, and the information about the electrostimulation configurations or the "shared electrodes" from the pacing information receiver 426. The rank order generation circuit 425 can perform multi-level ranking on the candidate sensing vectors, such as by generating first ranked vectors by ranking at least some of the candidate sensing vectors according to a first specified order of one or both of the respective signal intensity indicators and the respective interference indicators, and then generating second ranked vectors by ranking the first ranked vectors according to a second specified order based on the electrode information. In an example, the rank order generation circuit 425 can generate the first ranked vectors according to a descending order of the signal intensity indicators, or an ascending order of the interference indicators, and generate the second ranked vectors according an ascending order of the number of "shared electrodes" in the candidate sensing vector. In an example of ranking a plurality of LV sensing vectors $\{V_{xy}\}$ where x and y denotes the two sensing electrodes constituting the sensing vector $V_{xy}$, the rank order generation circuit 425 can generate a first-level ranked list $\{V_{xy}\}^1$ by ranking the candidate vectors $\{V_{xy}\}$ according to a descending order of the signal intensity indicators, then generate a second-level ranked list $\{V_{xy}\}^2$ by ranking $\{V_{xy}\}^1$ according to an ascending order of the noise or interference such as far-field atrial sensing. The second-level ranked list $\{V_{xy}\}^2$ can be screened to determine the number of "shared electrodes" involved in each sensing vector in $\{V_{xy}\}^2$. The rank order generation circuit 425 can perform a ranking according to an ascending order of the number of the "shared electrodes", such that the sensing vectors with no "shared electrode" have higher priority on the ranked vector list than the sensing vectors with only one "shared electrode", and the sensing vectors with both electrodes being "shared electrode" have the lowest priority. In some examples, for those sensing vectors that do not involve any "shared electrode", the rank order generation circuit 425 can rank the sensing vectors according to a descending order of the distance between a sensing electrode and the nearest stimulation electrode.

As an example, Table 1 illustrates a table of multi-level ranking of LV sensing vectors, such as presented in a display unit of a user interface. The signal intensity indicators include the intrinsic amplitude of LV activation obtained from the LV electrogram, and susceptibility to postures or activities which has a categorical value indicating the variability of the sensed intrinsic LV amplitude across different postures or activity levels. The noise or interference indicators include the SNR and the far-field atrial sensing, both having respective categorical values. The ranking also includes number of "shared electrodes" used for electrostimulation. The first-level ranking can be based on the signal intensity indicators, including a descending order of the intrinsic LV amplitude, followed by an ascending order of the susceptibility to postures or activities. The second-level ranking is based on the noise or interference indicator, including a descending order of SNR and an ascending order of presence or intensity of far-field atrial activities. The third-level ranking is based on an ascending order of the "shared electrode" in each of the sensing vectors.

TABLE 1

| LV sensing vectors | Composite score | Intrinsic LV Amplitude | Susceptibility to postures or activities | Signal-to-noise ratio (SNR) | Far-field atrial sensing | # of shared electrodes |
|---|---|---|---|---|---|---|
| LV1 - Can | 9 | 4.5 mV | Low | Low | Low | 0 |
| LV1-LV4 | 9 | 4.4 mV | Medium | Low | Low | 1 |
| LV2 - Can | 8 | 3.5 mV | Low | High | Medium | 1 |
| LV1-LV2 | 7 | 3.0 mV | High | Low | Medium | 1 |
| LV4 - Can | 4 | 2.9 mV | Medium | Medium | High | 1 |

Figure 5:
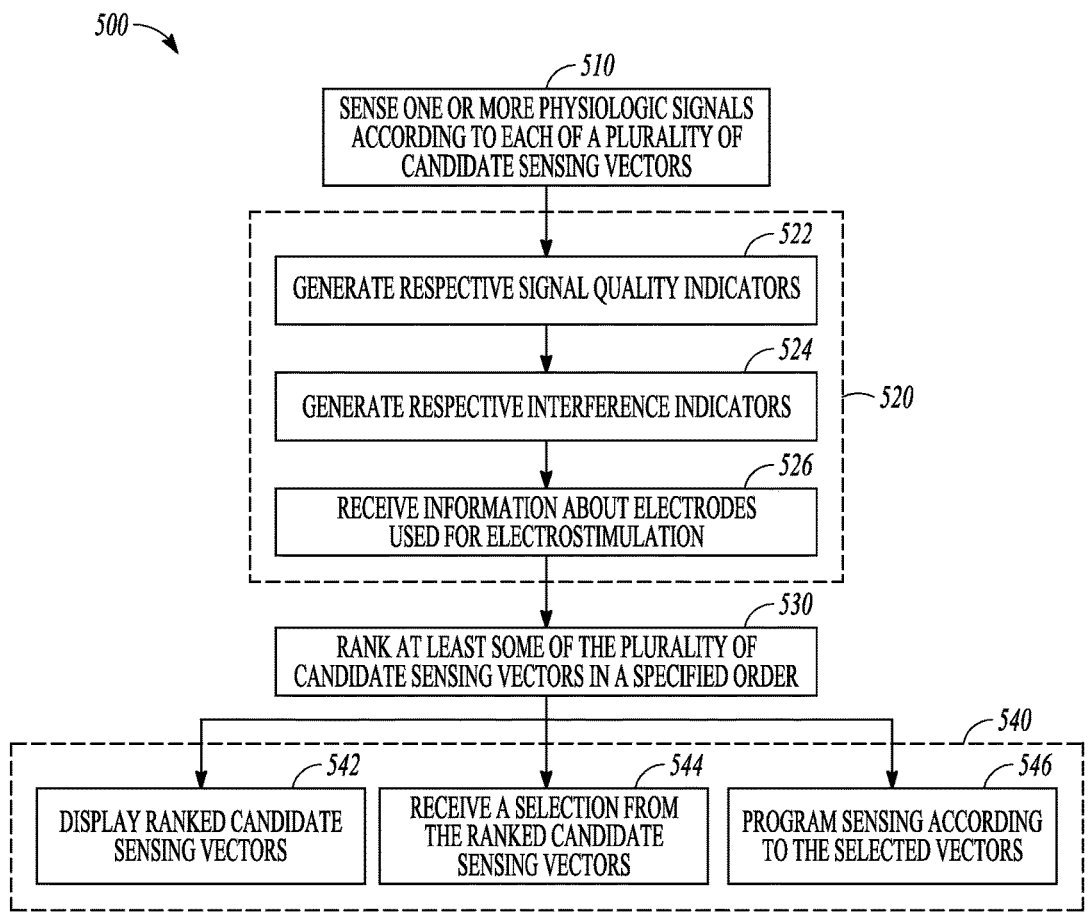
FIG. 5 illustrates generally an example of a method for evaluating multiple candidate sensing vectors for use in sensing cardiac electrical activity.

In addition to or in lieu of the multi-level ranking, the sensing vector assessment circuit 424 can use at least some of the signal intensity indicators, the noise or interference indicators, and the electrostimulation electrode information such as the number of "shared electrodes", to generate a composite score, such as illustrated in FIG. 5. A candidate sensing vector having a higher composite score can indicate a better overall sensing performance than a different candidate sensing vector having a lower composite score. The electrostimulation electrode information can be represented by a numerical or categorical penalty score based on the number of "shared electrodes" contained in each sensing vector. In an example, a higher penalty score can be assigned to a sensing vector with both electrodes being "shared electrodes" than a sensing vector with only one "shared electrode", and a sensing vector with no "shared electrodes" can have smallest penalty score (e.g., a penalty score of zero). A higher penalty score can reduce the composite score, and the sensing vector assessment circuit 424 can rank the candidate sensing vectors according to a descending order of the respective composite scores of the candidate sensing vectors. The composite score can be computed using a fusion of the signal intensity indicators and the noise or interference indicators. Examples of the fusion algorithm can include decision trees, weighted averages, and neural networks, among others. In some examples, the ranking of the candidate sensing vectors can be based on the composite score in a specified order.

FIG. 5 illustrates generally an example of a method 500 for evaluating a plurality of candidate sensing vectors for use in sensing cardiac electrical activity. The method 500 can be implemented and operate in an implantable, wearable, or other ambulatory medical device, or a programmer or a remote server-based patient management system in communication with the medical device. In an example, the method 500 can be used at device implant to automatically, or to allow a system user to manually, program an initial "optimal" sensing vector selected from the ranked list of candidate sensing vectors. In an example, the method 500 can be performed by the automatic sensing vector selection circuit 200, or any modification thereof.

The method 500 can begin at step 510, where one or more physiologic signals can be sensed. The sensed physiologic signals can be indicative of target cardiac electrical activity, and can include one or more of surface electrocardiograms (ECGs), subcutaneous ECGs, or intracardiac electrograms (EGMs) sensed by using intracardiac electrodes such as those on the implantable leads 108A-C or the can 112. In an example, the physiologic signals can include LV EGMs sensed using a plurality of LV sensing vectors. Each LV sensing vector can include at least one electrode positioned at or close to the LV, such as the electrodes 161-164. The LV sensing vectors can include unipolar or bipolar LV sensing vectors. A unipolar LV sensing vector can involve one LV electrode and the IMD can 112. A bipolar LV sensing vector can involve two LV electrodes such as any two of the electrodes 161-164, or an LV electrode and another electrode positioned on a different chamber or on a different lead, such as one of electrodes 152-155 on the RV lead 108B, or electrodes 141 or 142 on the RA lead 108A.

At 520, a plurality of candidate sensing vectors can be evaluated using the physiologic signals sensed when the electrostimulation is delivered using each of the plurality of candidate sensing vectors. As illustrated in FIG. 5, the evaluation of the candidate sensing vectors can include several steps 522, 524 and 526.

At 522, respective signal intensity indicators, which are indicative of the strength of the sensed physiologic signals, can be generated. The signal intensity indicator can be generated based on one or more signal metrics derived from the physiological signals. The signals metrics can be temporal or morphological features including intensities (such as amplitudes) and timing of P wave, Q wave, R wave, QRS complex, or T wave detected from a surface ECG or a subcutaneous ECG; timing of sensed activation of at least a portion of a chamber of the heart such as RA, RV, and LV, obtained from the intracardiac EGMs; QRS width; electrical delay of a chamber of the heart such as LV electrical delay; interventricular conduction delay such as LV-RV delay; intraventricular delay; Q wave to left ventricle activation (Q-LV) interval; among others.

The signal intensity indicator can include statistics of a signal metric computed using multiple measurements of the signal metric over a specified period of time or over a specified number of cardiac cycles. In an example, the signal intensity indicator can include a mean, median, mode, or other measures of central tendency measure, or variability, computed over multiple measurements of the signal metric. In some examples, the signal metric can be obtained when a specified condition is met, such as when the heart undergoes normal sinus rhythm or when the heart rate is within a specified range. In some examples, the signal intensity indicator can further include a posture or physical activity indicated signal metric, which can be indicative of robustness of the sensing vector in sensing the cardiac electrical activity under different postures or levels of physical activities. The posture or physical activity indicated signal metric can be computed as a variability measure of the signal metric using multiple measurements respectively obtained across multiple physical activity levels or postures.

At 524, respective noise or interference indicators, which are indicative of presence or degree of interference produced by an activity other than the target cardiac electrical activity, can be generated. The noise indicators can include one or more of a noise level metric such as noise amplitude, a signal-to-noise ratio (SNR), or presence or intensity of far-field electrical activity of a portion of the heart different than the target cardiac electrical activity. In an example of ranking multiple candidate LV sensing vectors, the cross-channel interference can include presence or intensity of far-field atrial activation detected in the LV electrogram.

At 526, information about electrodes used for electrostimulation can be received, such as provided by a system user or from a memory storing device programming information. To minimize the interference caused by after-potential of the stimulation pulses and electrode-tissue polarization artifact, it is desirable that the sensing vector do not include "shared electrodes" also used for delivering electrostimulation. For each of the candidate sensing vectors, the information about electrodes used for electrostimulation can include: the number of "shared electrodes"; the role of the electrode in the electrostimulation vector configuration (e.g., whether the "shared electrode" is used as a cathode or anode for electrostimulation) or the distance between the electrodes involved in the sensing vector and the nearest stimulation electrode involved in an electrostimulation vector if the candidate sensing vector does not involve any "shared electrode".

At 530, at least some of the plurality of candidate sensing vectors can be ranked according to a specified order using the respective signal intensity indicators and the respective noise or interference indicators, or additionally using the information about electrodes used for electrostimulation. The ranking can be performed using a multi-level ranking method, including generating first ranked vectors by ranking at least some of the plurality of candidate sensing vectors according to a first specified order of one or both of the respective signal intensity indicators and the respective interference indicators, identifying a portion of the first ranked vectors with corresponding respective signal intensity indicators or corresponding respective interference indicators meeting a specified condition, and generating second ranked vectors by ranking the identified portion of the first ranked vectors according to a second specified order based on the electrode information. In an example, the first ranked vectors can be generated according to a descending order of the signal intensity indicators or an ascending order of the interference indicators, and the second ranked vectors can be generated according an ascending order of the number of electrodes also used for delivering cardiac electrostimulation.

The candidate sensing vectors can alternatively be ranked based on a composite score computed using at least some of the signal intensity indicators and the noise or interference indicators, or additionally the electrostimulation electrodes information. In an example, each signal metric can be assigned a numerical or categorical score indicative of sensing efficacy, and the composite score can then be computed using a fusion of the scores of the signal metrics. In another example, two or more signal metrics associated with signal quality can be combined to form an aggregated score of signal intensity indicator, and two or more metrics associated with noise or interference can be combined to form an aggregated score of noise or interference indicator. The aggregated score of signal intensity indicator and the aggregated score of noise or interference indicator can each have a respective numerical value, and the composite score can then be computed using a fusion of the aggregated score of signal intensity indicators and the aggregated score of noise or interference indicators. Examples of the fusion algorithm can include decision trees, weighted averages, neural networks, or any other linear or non-linear algorithms.

At 540, the ranked candidate sensing vectors can be used in one or more processes including information presentation, sensing vector recommendation, or programming of sensing vectors. Step 542 involves displaying on a user interface the ranked sensing vectors, and one or more of the signal intensity indicators, the noise or interference indicators, or the electrostimulation electrodes information. The ranked sensing vectors and the relevant information can be presented in a textual, tabular, or graphical format such as a table, a chart, or a diagram, among others. Additionally or alternatively, at 544, a user's selection of one or more sensing vectors from the ranked sensing vectors can be received, such as via a user input device. The user can program the sensing circuit using the selected one or more vectors. Step 546 involves an alternative or additional process of automatically selecting at least one sensing vector from the ranked sensing vectors and programmed it into the sensing circuit for sensing cardiac electrical activity.

Figure 6:
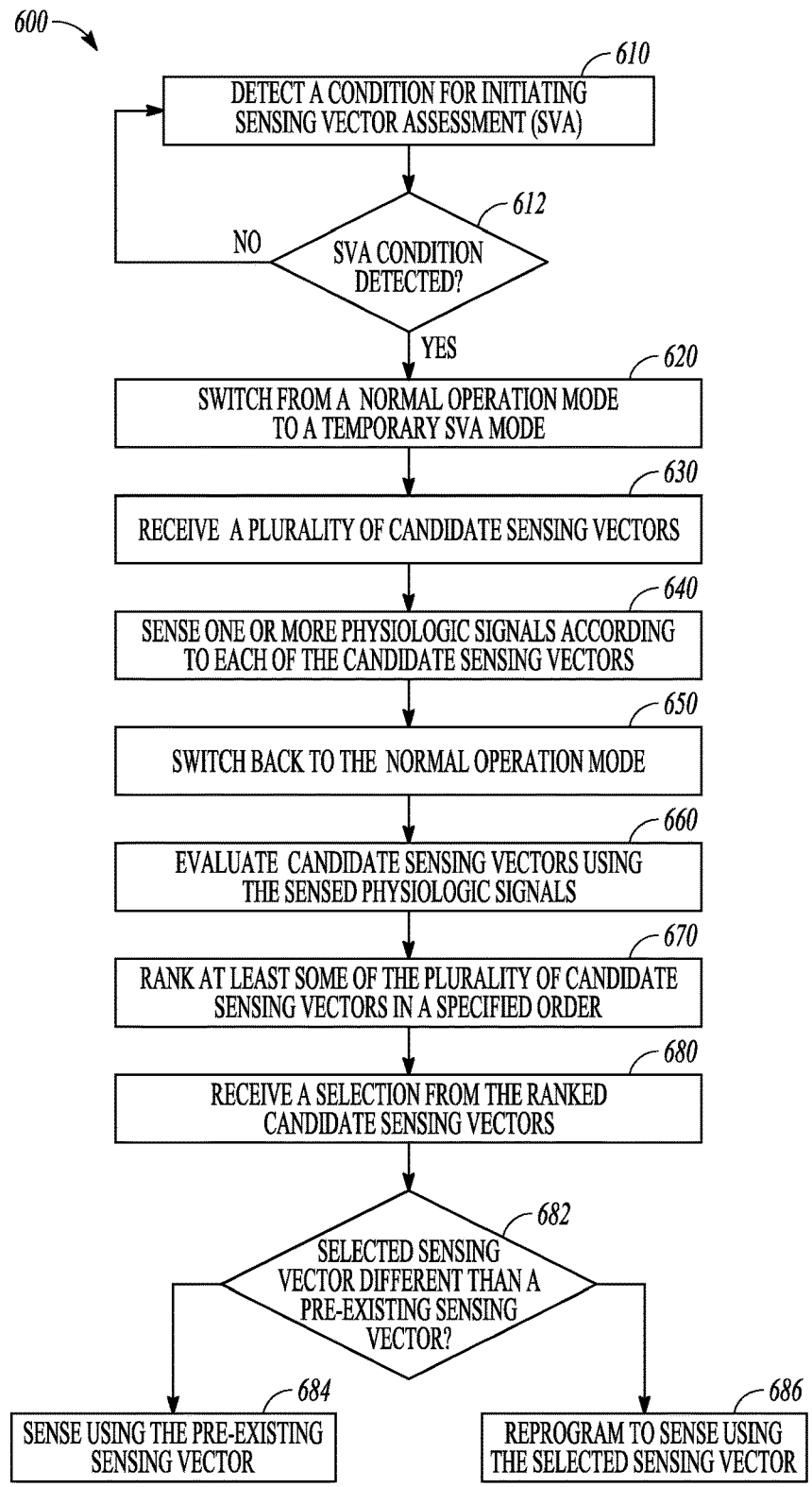
FIG. 6 illustrate generally an example of a method for operating an implantable medical device for automatic sensing vector switching.

FIG. 6 illustrates generally an example of a method 600 for operating an implantable medical device (IMD) for automatic sensing vector switching. The method 600 can be used in post-implant device reprogramming, including switching from a pre-existing sensing vector to a different sensing vector if the latter provides better performance such as higher signal quality, more reliable and consistent cardiac event sensing, less noise or interference, less susceptibility to changes in posture or physical activity level, etc. In an example, the method 600 can be performed by the automatic sensing vector selection circuit 200, or any modification thereof.

At 610, a detection of a condition to initialize sensing vector assessment (SVA) process can be routinely performed. Such a condition can be a clinical or environmental event that is likely to affect the sensing of the cardiac electric activity using a pre-existing sensing vector. Examples of the clinical or environmental event can include device or lead revision, changes in electrode-tissue interface such as due to growth of fibrous tissue or scar tissue around the electrode, lead integrity, lead/electrode migration or dislodgement, progression of cardiac disease or change in health condition, change of device programming such as LV pacing vectors or mode of pacing, among others. At 612, if one or more such clinical or environmental events have been detected, or upon receipt of a user command for conducting a SVA process, the SVA process can be initiated. At 620, the IMD can be programmed to temporarily switching from a normal operation mode to a temporary SVA test mode. The SVA test mode can include suspension of cardiac pacing therapies or change of diagnostic parameters in order to properly sense intrinsic cardiac activities.

At 630, a plurality of candidate sensing vectors can be received, such as from a memory that stores the pre-determined candidate sensing vectors, or from a system user such as via the user interface unit 250. In an example, the candidate sensing vectors can include a plurality of unipolar and bipolar LV sensing vectors. One or more physiologic signals indicative of target cardiac electrical activity can be sensed using each of the candidate sensing vectors at 640, which may involve a process similar to step 510 of the method 500. Then at 650, the IMD can be programmed back to the normal operation mode. At 660, the candidate sensing vectors can be assessed using the respective one or more physiologic signals, including generating respective signal intensity indicators, the respective noise or interference indicators, and the information about electrodes used for electrostimulation, a process similar to step 520 of the method 500. Following similar processes at steps 530 and 544, at least some of the plurality of candidate sensing vectors can be ranked in a specified order at 670, and at least one vector can be selected from the ranked sensing vectors at 680. The selected sensing vector can then be compared to the pre-existing sensing vector at 682. If the selected sensing vector differs from the pre-existing sensing vector, then at 686 the selected sensing vector can be programmed to the IMD to replace the pre-existing sensing vector to sense future cardiac electrical activity. Additional confirmation by the system user can also be required before performing the sensing vector switch. However, if the selected sensing vector is the same as the pre-existing sensing vector, or if the selected vector switch is not confirmed by the system user, then at 684 the pre-existing sensing vector can continue to be used cardiac electrical activity.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for evaluating a plurality of candidate sensing vectors for use in sensing electrical activity of a heart, the system comprising:
    a sensing circuit configured to sense one or more physiologic signals indicative of target cardiac electrical activity according to a specified sensing vector involving first and second electrodes;
    a signal processor circuit, configured to generate a signal intensity indicator and an interference indicator using the one or more physiologic signals, the signal intensity indicator indicative of the strength of the sensed one or more physiologic signals, the interference indicator indicative of presence or degree of interference produced by an activity other than the target cardiac electrical activity;
    a sensing vector assessment circuit, included in or communicatively coupled to the signal processor circuit, configured to:
        for the plurality of candidate sensing vectors, receive respective signal intensity indicators and respective interference indicators;
        for the plurality of candidate sensing vectors, receive respective electrode information about first and second electrodes of the corresponding candidate sensing vector, the respective electrode information including the respective first or second electrode also used for delivering cardiac electrostimulation; and
        produce a rankable set of at least some of the plurality of candidate sensing vectors using the respective signal intensity indicators, the respective interference indicators, and the respective electrode information; and
    a user interface unit configured to:
        display the ranked sensing vectors, the corresponding respective signal intensity indicators, and the corresponding respective interference indicators; and
        receive a user input, including selecting at least one sensing vector from the ranked sensing vectors and programming the sensing circuit to sense the target cardiac electrical activity using the selected at least one sensing vector.

2. The system of claim 1, wherein the sensing vector assessment circuit is configured to rank at least some of the plurality of candidate sensing vectors including:
    generating first ranked vectors by ranking the at least some of the plurality of candidate sensing vectors according to a first specified order of one or both of the respective signal intensity indicators and the respective interference indicators;
    identifying a portion of the first ranked vectors with corresponding respective signal intensity indicators or corresponding respective interference indicators meeting a specified condition; and
    generating second ranked vectors by ranking the identified portion of the first ranked vectors according to a second specified order based on the respective electrode information.

3. The system of claim 2, wherein the sensing vector assessment circuit is configured to generate the first ranked vectors according to a descending order of the respective signal intensity indicators or an ascending order of the respective interference indicators.

4. The system of claim 2, wherein the sensing vector assessment circuit is configured to generate the second ranked vectors according an ascending order of the number of electrodes also used for delivering cardiac electrostimulation.

5. The system of claim 1, wherein the sensing vector assessment circuit is configured to:
    for at least some of the plurality of candidate sensing vectors, generate respective composite scores using the respective signal intensity indicators, the respective interference indicators, and the respective electrode information; and
    rank the at least some of the plurality of candidate sensing vectors in a specified order of the respective composite scores.

6. A system for evaluating a plurality of candidate sensing vectors for use in sensing electrical activity of a heart, the system comprising:
    a sensing circuit configured to sense one or more physiologic signals indicative of target cardiac electrical activity according to a specified sensing vector involving first and second electrodes;
    a signal processor circuit, configured to generate a signal intensity indicator and an interference indicator using the one or more physiologic signals, the signal intensity indicator indicative of the strength of the sensed one or more physiologic signals, the interference indicator indicative of presence or degree of interference produced by an activity other than the target cardiac electrical activity; and a sensing vector assessment circuit, included in or communicatively coupled to the signal processor circuit, configured to:
for the plurality of candidate sensing vectors, receive respective signal intensity indicators and respective interference indicators;
for the plurality of candidate sensing vectors, receive respective electrode information about first and second electrodes of the corresponding candidate sensing vector, the respective electrode information including the respective first or second electrode also used for delivering cardiac electrostimulation;
produce a rankable set of at least some of the plurality of candidate sensing vectors using the respective signal intensity indicators, the respective interference indicators, and the respective electrode information; and
automatically select at least one sensing vector from the ranked sensing vectors; and
wherein the sensing circuit is configured to sense the target cardiac electrical activity according to the selected at least one sensing vector.

7. The system of claim 1, further comprising a therapy circuit configured to deliver a therapy using the ranked candidate sensing vectors.

8. The system of claim 1, further comprising a sensor configured to sense a physical activity level or a posture of a patient, wherein the signal processor circuit is configured to generate the variability of the signal metric during multiple physical activity levels or postures.

9. The system of claim 1, wherein the signal processor circuit is configured to generate the interference indicators including one or more of a noise level, a signal-to-noise ratio (SNR), or presence or intensity of far-field electrical activity of a portion of the heart.

10. The system of claim 1, wherein the plurality of candidate sensing vectors include two or more LV sensing vectors each involving at least one electrode removably and respectively, positionable at an LV of the heart, wherein the sensing circuit is configured to sense respective LV electrograms using the two or more LV sensing vectors.

11. The system of claim 10, wherein the sensing vector assessment circuit is configured to:
generate the first ranked vectors according to one or both of a descending order of the signal intensity indicators and an ascending order of the interference indicators; and
generate the second ranked vectors according to an ascending order of the number of electrodes also used for delivering cardiac electrostimulation to the LV.

12. A method for operating a medical system to evaluate a plurality of candidate sensing vectors for use in sensing electrical activity of a heart, comprising:
sensing, using a sensing circuit; one or more physiologic signals indicative of target cardiac electrical activity according to each of the plurality of candidate sensing vectors involving first and second electrodes;
for the plurality of candidate sensing vectors, generating respective signal intensity indicators and respective interference indicators using a signal processor circuit using the one or more physiologic signals, the respective signal intensity indicators indicative of the strength of the sensed one or more physiologic signals, the respective interference indicators indicative of presence or degree of interference produced by an activity other than the target cardiac electrical activity;
for the plurality of candidate sensing vectors, receiving respective electrode information about first and second electrodes of the corresponding candidate sensing vector using a sensing vector assessment circuit, the respective electrode information including the first or second electrode also used for delivering cardiac electrostimulation; and
ranking at least some of the plurality of candidate sensing vectors using the sensing vector assessment circuit using the respective signal intensity indicators, the respective interference indicators, and the respective electrode information.

13. The method of claim 12, wherein ranking at least some of the plurality of candidate sensing vectors includes:
generating first ranked vectors by ranking the at least some of the plurality of candidate sensing vectors according to a first specified order of one or both of the respective signal intensity indicators and the respective interference indicators; and
identifying a portion of the first ranked vectors with corresponding respective signal intensity indicators or corresponding respective interference indicators meeting a specified criterion;
generating second ranked vectors by ranking the identified portion of the first ranked vectors according to a second specified order based on the electrode information.

14. The method of claim 12, wherein ranking at least some of the plurality of candidate sensing vectors includes:
for at least some of the plurality of candidate sensing vectors, generating respective composite scores using the respective signal intensity indicators, the respective interference indicators, and the respective electrode information; and
ranking the at least some of the plurality of candidate sensing vectors in a specified order of the respective composite scores.

15. The method of claim 12, further comprising:
displaying in a user interface unit the ranked sensing vectors, the corresponding respective signal intensity indicators, and the corresponding respective interference indicators; and
receiving a user input, including selecting at least one sensing vector from the ranked sensing vectors and programming the sensing circuit to sense the target cardiac electrical activity according to the selected at least one sensing vector.

16. The method of claim 12, wherein generating the respective signal intensity indicators includes producing at least a signal metric using the one or more physiologic signals, and determining one or more of a central tendency measure, or a variability, of the signal metric over a specified period of time.

17. The method of claim 16, further comprising sensing a physical activity level or a posture of a patient, wherein generating the respective signal intensity indicators includes generating the variability of the signal metric during multiple physical activity levels or postures.

18. The method of claim 12, wherein generating the respective interference indicators includes determining one or more of a noise level, a signal-to-noise ratio (SNR), or presence or intensity of far-field electrical activity of a portion of the heart.

19. The method of claim 12, wherein the plurality of candidate sensing vectors include two or more LV sensing vectors each involving at least one electrode removably and respectively positionable at an LV of the heart, wherein:
  sensing the one or more physiologic signals includes sensing respective LV electrograms using the two or more LV sensing vectors; and
  ranking at least some of the plurality of candidate sensing vectors includes generating the first ranked vectors according to one or both of a descending order of the signal intensity indicators and an ascending order of the interference indicators, and generating the second ranked vectors according to an ascending order of the number of electrodes also used for delivering cardiac electrostimulation to the LV.

* * * * *